(12) United States Patent
Westerhoff et al.

(10) Patent No.: US 11,085,906 B2
(45) Date of Patent: Aug. 10, 2021

(54) DRY REAGENT COLORIMETRIC SENSING OF NANOPARTICLES IN AQUEOUS MEDIA

(71) Applicants: Paul K. Westerhoff, Scottsdale, AZ (US); Xiangyu Bi, Tempe, AZ (US); Shahnawaz Sinha, Chandler, AZ (US); Jonathan D. Posner, Seattle, WA (US); Charlie Corredor, Seattle, WA (US)

(72) Inventors: Paul K. Westerhoff, Scottsdale, AZ (US); Xiangyu Bi, Tempe, AZ (US); Shahnawaz Sinha, Chandler, AZ (US); Jonathan D. Posner, Seattle, WA (US); Charlie Corredor, Seattle, WA (US)

(73) Assignees: Arizona Board of Regents on behalf of Arizona State University, Scottsdale, AZ (US); University of Washington, Seattle, WA (US)

( * ) Notice: Subject to any disclaimer, the term of this patent is extended or adjusted under 35 U.S.C. 154(b) by 497 days.

(21) Appl. No.: 15/999,043

(22) Filed: Aug. 17, 2018

(65) Prior Publication Data
US 2019/0056363 A1 Feb. 21, 2019

Related U.S. Application Data

(60) Provisional application No. 62/547,671, filed on Aug. 18, 2017.

(51) Int. Cl.
*G01N 31/22* (2006.01)
*B82Y 35/00* (2011.01)
(Continued)

(52) U.S. Cl.
CPC ............ *G01N 31/22* (2013.01); *G01N 21/78* (2013.01); *B82Y 35/00* (2013.01); *G01N 2015/0038* (2013.01)

(58) Field of Classification Search
CPC ........ G01N 21/77; G01N 21/78; G01N 31/22; G01N 2015/0038; B82Y 35/00
See application file for complete search history.

(56) References Cited

U.S. PATENT DOCUMENTS

| | | |
|---|---|---|
| 9,751,785 B2 | 9/2017 | Doudrick et al. |
| 2013/0175220 A1 | 7/2013 | Hristovski et al. |

(Continued)

OTHER PUBLICATIONS

Supporting Information for Corredor, C. et al. "Colorimetric Detection of Catalytic Reactivity of Nanoparticles in Complex Matrices," Environ. Sci. Technol. 2015, 49, 6, 3611-3618 (Year: 2015).*

(Continued)

*Primary Examiner* — Christopher Adam Hixson
*Assistant Examiner* — Michelle Adams
(74) *Attorney, Agent, or Firm* — Fish & Richardson P.C.

(57) ABSTRACT

A composition for dry reagent colorimetric sensing of nanoparticles in aqueous media, including sodium borohydride (NaBH$_4$), methylene blue (MB), and 4-(2-hydroxyethyl)-1-piperazineethanesulfonic acid (HEPES) in the form of a powdered mixture. The composition may be formed by combining MB, HEBES, and water to yield an aqueous mixture, removing water from the aqueous mixture to yield a solid mixture, and combining NaBH$_4$ powder with the solid mixture to yield the composition. The composition may be used to detect metallic nanoparticles an aqueous solution by combining the composition with an aqueous solution to yield a test solution, and assessing a concentration of the metallic nanoparticles in the test solution based on absorbance of light by the test solution. The composition may be provided in an assay kit for sensing nanoparticles in aqueous media.

20 Claims, 5 Drawing Sheets

(51) Int. Cl.
G01N 21/77 (2006.01)
G01N 21/78 (2006.01)
G01N 15/00 (2006.01)

(56) References Cited

U.S. PATENT DOCUMENTS

| | | | |
|---|---|---|---|
| 2016/0334311 | A1 | 11/2016 | Westerhoff et al. |
| 2017/0313601 | A1 | 11/2017 | Westerhoff et al. |
| 2018/0080148 | A1 | 3/2018 | Westerhoff et al. |
| 2018/0085800 | A1 | 3/2018 | Westerhoff et al. |
| 2018/0086648 | A1 | 3/2018 | Hristovski et al. |
| 2018/0319677 | A1 | 11/2018 | Perreault et al. |
| 2019/0094118 | A1 | 3/2019 | Westerhoff et al. |
| 2019/0218128 | A1 | 7/2019 | Apul et al. |

OTHER PUBLICATIONS

Corredor, C. "Methods to Assess Presence and Biological Impact of Engineered Nanoparticles," Ph.D. Dissertation, University of Washington 2015. (Year: 2015).*

Speed, D. et al. "Physical, Chemical, and In Vitro Toxicological Characterization of Nanoparticles in Chemical Mechanical Planarization Suspensions Used in the Semiconductor Industry: Towards Environmental Health and Safety Assessments," Environ. Sci.: Nano, 2015, 2, 227; ESI (Year: 2015).*

Supporting Information for Gilbertson, L.M. et al. "Shape-Dependent Surface Reactivity and Antimicrobial Activity of Nano-Cupric Oxide," Environ. Sci. Technol. 2016, 50, 7, 3975-3984. (Year: 2016).*

Bi, X. and Westerhoff, P.K. "Development of a powder assay kit to fast detect gold nanoparticles in aquatic media," Abstracts of Papers, 254th ACS National Meeting & Exposition, Washington, DC, USA, Aug. 20-24, 2017 (Year: 2017).*

Bi, X. "Detection and Surface reactivity of Engineered Nanoparticles in Water," Ph.D. Dissertation, Arizona State University 2018. (Year: 2018).*

Carregal-Romero et al, "Colloidal Gold-Catalyzed Reduction of Ferrocyanate (III) by Borohydride Ions: A Model System for Redox Catalysis". Langmuir 2010, 26, 2, 1271-1277. https://doi.org/10.1021/la902442p.

Chamoun et al, "Co-alpha Al(2)O(3)—Cu as shaped catalyst in NaBH(4) hydrolysis". Int J Hydrogen Energ 2010, 35, (13), pp. 6583-6591.

Chatterjee et al, "Selective Fluorogenic and Chromogenic Probe for Detection of Silver Ions and Silver Nanoparticles in Aqueous Media". Journal of the American Chemical Society 2009, 131, (6), pp. 2040-2041.

Corma et al, "Supported gold nanoparticles as catalysts for organic reactions". Chem Soc Rev 2008, 37, (9), 2096-2126.

Corredor et al, "Colorimetric Detection of Catalytic Reactivity of Nanoparticles in Complex Matrices". Environ. Sci. Technol. 2015, 49, (6), 3611-3618.

Daniel et al. "Assembly, supramolecular chemistry, quantum-size-related properties, and applications toward biology, catalysis, and nanotechnology". Chemical Reviews 2004, 104, (1), 293-346.

De Corte et al, "Biosupported Bimetallic Pd—Au Nanocatalysts for Dechlorination of Environmental Contaminants". Environ. Sci. Technol. 2011, 45, (19), 8506-8513.

Denuault et al, "Direct Determination of Diffusion-Coefficients by Chronoamperometry at Microdisk Electrodes". J Electroanal Chem 1991, 308, (1-2), 27-38.

DeTacconi et al, "Reversibility of photoelectrochromism at the TiO2/methylene blue interface". Journal of the Electrochemical Society 1997, 144, (7), 2486-2490.

Esumi et al, "Preparation of PAMAM- and PPI-Metal (silver, platinum, and palladium) Nanocomposites and Their Catalytic Activities for Reduction of 4-Nitrophenor". Langmuir 2004, 20, (1), 237-243.

Freund et al, "Catalysis by Colloidal Gold of the Reaction between Ferricyanide and Thiosulfate Ions". J Chem Soc Farad T 1 1986, 82, 2277-2282.

Galagan et al, "Reversible photoreduction of methylene blue in acrylate media containing benzyl dimethyl ketal". J Photoch Photobio A 2008, 195, (2-3), 378-383.

Gangula et al, "Catalytic Reduction of 4-Nitrophenol Using Biogenic Gold and Silver Nanoparticles Derived from Breynia Rhamnoides". Langmuir 2011, 27, (24), 15268-15274.

Gilbertson et al, "Shape-Dependent Surface Reactivity and Antimicrobial Activity of Nano-Cupric Oxide". Environ. Sci. Technol. 2016, 50, (7), 3975-3984.

Henglein "Catalysis of the reduction of thallium (1+) and of dichloromethane by colloidal silver in aqueous solution". Journal of Physical Chemistry 1979, 83, (22), 2858-2862.

Henglein "Reactions of Organic Free-Radicals at Colloidal Silver in Aqueous-Solution—Electron Pool Effect and Water Decomposition". Journal of Physical Chemistry 1979, 83, (17), 2209-2216.

Henglein et al, "Storage of Electrons in Aqueous-Solution—the Rates of Chemical Charging and Discharging the Colloidal Silver Microelectrode". Journal of the American Chemical Society 1981, 103, (5), 1059-1066.

Herves et al, "Catalysis by Metallic Nanoparticles in Aqueous Solution: Model Reactions". Chem Soc Rev 2012, 14, (17), 5577-5587.

Impert et al, "Kinetics and mechanism of a fast leuco-Methylene Blue oxidation by copper(II)-halide species in acidic aqueous media". Dalton T 2003, (3), 348-353.

Leaist "The Effects of Aggregation, Counterion Binding, and Added Nacl on Diffusion of Aqueous Methylene-Blue". Can J Chem 1988, 66, (9), 2452-2457.

Levy et al, "A Practical Controlled Source of Hydrogen—Catalyzed Hydrolysis of Sodium Borohydride". Ind Eng Chem 1960, 52, (3), 211-214.

Li et al, "Mechanism of Photogenerated Reactive Oxygen Species and Correlation with the Antibacterial Properties of Engineered Metal-Oxide Nanoparticles". Acs Nano 2012, 6, (6), 5164-5173.

Liu et al, "A review of anode catalysis in the direct methanol fuel cell". J Power Sources 2006, 155, (2), 95-110.

Miller et al, "Catalytic Water Reduction at Colloidal Metal Microelectrodes .2. Theory and Experiment". Journal of the American Chemical Society 1981, 103, (18), 5336-5341.

Mills et al, "Photobleaching of methylene blue sensitised by TiO 2: an ambiguous system?" Journal of Photochemistry and Photobiology A: Chemistry 1999, 127, (1), 123-134.

NanoComposix "NanoXact Certificate of Analysis" 1 of 3 https://tools.nanocomposix.com:48/cdn/coa/Gold/Spheres/NanoXact/AU20-NX-TA-ECP1499.pdf?2011853. Lot No. ECP1499. (Jul. 2020).

NanoComposix "NanoXact Certificate of Analysis" 2 of 3 https://tools.nanocomposix.com:48/cdn/coa/Gold/Spheres/NanoXact/AU50-NX-TA-SCM0018.pdf?2011844. Lot No. SCM0018. (Jul. 2020).

NanoComposix "NanoXact Certificate of Analysis" 3 of 3 https://tools.nanocomposix.com:48/cdn/coa/Gold/Spheres/NanoXact/AU80-NX-TA-DAC1070.pdf?2011925. Lot No. DAC1070. (Jul. 2020).

Narayanan et al, Effect of Catalysis on the Stability of Metallic Nanoparticles: Suzuki Reaction Catalyzed by PVP-Palladium Nanoparticles. Journal of the American Chemical Society 2003, 125, (27), 8340-8347.

Nigra et al. "Identification of site requirements for reduction of 4-nitrophenol using gold nanoparticle catalysts". Catalysis Science & Technology, 3(11), 2976-2983. (2013).

Nutt et al, "Designing Pd-on-Au bimetallic nanoparticle catalysts for trichloroethene hydrodechlorination". Environ. Sci. Technol. 2005, 39, (5), 1346-1353.

Pecsok "Polarographic Studies on the Oxidation and Hydrolysis of Sodium Borohydride". Journal of the American Chemical Society 1953, 75, (12), 2862-2864.

Pradhan et al, "Silver nanoparticle catalyzed reduction of aromatic nitro compounds". Colloid Surf. A-Physicochem. Eng. Asp. 2002, 196, (2-3), 247-257.

Singh et al, "Room-Temperature Hydrogen Generation from Hydrous Hydrazine for Chemical Hydrogen Storage". Journal of the American Chemical Society 2009, 131, (29), 9894-9895.

(56) References Cited

OTHER PUBLICATIONS

Spiro "Heterogeneous Catalysis in Solution .17. Kinetics of Oxidation-Reduction Reactions Catalyzed by Electron-Transfer through the Solid—Electrochemical Treatment". J Chem Soc Farad T 1 1979, 75, 1507-1512.

Wang et al, "Performance of the Supported Coper Oxide Catalysts for the Catalytic Incineration of Aromatic Hydrocarbons". Chemosphere 2006, 64, (3), 503-509.

Wunder et al, "Catalytic Activity of Faceted Gold Nanoparticles Studied by a Model Reaction: Evidence for Substrate-Induced Surface Restructuring". Acs Catal 2011, 1, (8), 908-916.

Yang et al, "A Facile One-Step Way to Anchor Noble Metal (Au, Ag, Pd) Nanoparticles on a Reduced Graphene Oxide Mat with Catalytic Activity for Selective Reduction of Nitroaromatic Compounds". Crystengcomm 2013, 15 (34), 6819-6828.

\* cited by examiner

DRY REAGENT COLORIMETRIC SENSING OF NANOPARTICLES IN AQUEOUS MEDIA

CROSS-REFERENCE TO RELATED APPLICATION

This application claims the benefit of U.S. Application No. 62/547,671 entitled "DRY REAGENT COLORIMETRIC SENSING OF NANOPARTICLES IN AQUEOUS MEDIA" and filed on Aug. 18, 2017, which is incorporated by reference herein in its entirety.

STATEMENT OF GOVERNMENT INTEREST

This invention was made with government support under 1449500 awarded by the National Science Foundation. The government has certain rights in the invention.

TECHNICAL FIELD

This invention relates to dry reagent colorimetric sensing of nanoparticles in aqueous media.

BACKGROUND

Engineered nanoparticles (NPs) are widely used in industrial and commercial products (e.g., catalyst composites, coatings, and medicine), and their accidental release into aqueous media in the environment is possible. Tracking NPs in water systems is a need for assessing their exposure and risks. Existing techniques for detecting NPs in natural waters are often costly and/or time consuming, or both. For example, techniques based on inductively coupled plasma mass spectroscopy (ICP-MS), including single particle-, flow field fractionation-, and high pressure liquid chromatography (HPLC)-ICP-MS, have complicated and expensive setups. Transmission electron microscopy (TEM) can characterize NP size and morphology, but it is costly, laborious, and difficult to deduce low abundance or concentration in an environmental sample. Some techniques have thus been employed to extract low-concentration NPs from liquids (e.g., "cloud-point extraction") prior to analysis. However, rapid and economic detection of NPs in water was not satisfactorily achieved.

SUMMARY

In a first general aspect, a composition for dry reagent colorimetric sensing of nanoparticles in aqueous media includes sodium borohydride ($NaBH_4$), methylene blue (MB), and 4-(2-hydroxyethyl)-1-piperazineethanesulfonic acid (HEPES) in the form of a powdered mixture. In a second general aspect, composition is be formed by combining MB, HEBES, and water to yield an aqueous mixture, removing water from the aqueous mixture to yield a solid mixture, and combining $NaBH_4$ powder with the solid mixture to yield the composition. In a third general aspect, metallic nanoparticles an aqueous solution are detected by combining the composition with an aqueous solution to yield a test solution, and assessing a concentration of the metallic nanoparticles in the test solution based on absorbance of light by the test solution. In a fourth general aspect, an assay kit includes a vial and the composition of the first general aspect.

Implementations of the first through fourth general aspects may include one or more of the following features.

A molar ratio of $NaBH_4$:HEPES:MB is about 500:500:1. The composition may further include a base, such as sodium hydroxide. The composition, when dissolved in water, typically has a pH of about 7.

Implementations of the third general aspect may include one or more of the following features.

Assessing the concentration of the metallic nanoparticles in the test solution may occur less than about five minutes (e.g., about two minutes) after combining the composition with the sample of the aqueous media. A concentration of MB in the test solution is about 20 µM. A concentration of HEPES in the test solution is about 10 mM. A concentration of the $NaBH_4$ in the test solution is about 10 mM. Assessing the concentration of metallic nanoparticles includes assessing a concentration in range of about 5 µg/L to about 500 µg/L or greater for 5-nm gold nanoparticles, where the concentration of 5 µg/L for 5-nm gold nanoparticles is equivalent to a reactive nanoparticle surface area of about 0.3 $m^2/m^3$. Assessing the concentration of the metallic nanoparticles typically includes comparing the absorbance of light having a wavelength of 663 nm by the test solution with the absorbance of light having a wavelength of 663 by solutions having known concentrations of the metallic nanoparticles. The metallic nanoparticles catalyze the reduction of MB to leuco methylene blue (LMB).

This assay can be an efficient alternative for advanced and expensive instrumentation (e.g., ICP-MS), providing capital and time savings. Applications include monitoring the release of metallic NPs from commercial and industrial products (e.g., fabrics and NP-embedded membranes) into water.

DETAILED DESCRIPTION

A colorimetric powder assay kit for rapidly detecting metallic nanoparticles (NPs) in aqueous media is described. As used herein, a "powder assay," "powder assay kit," or "assay kit" generally refer to a chemical composition (e.g., a powdered mixture), selected to react with a detecting target such that a colorimetric property of the reactant or product (e.g., assessed via absorbance or fluorescence) is related to the target's concentration. "Metallic NPs" include metal NPs (e.g., gold, silver, platinum, and palladium NPs) and metal-containing NPs (e.g., metal oxides, such as copper oxide). These assay kits serve as reliable screening-level techniques to monitor metallic NPs in aqueous media. Powder assay kits for metallic NP detection described herein are designed to exploit a chemical reaction in which the targeted NP participates.

In one application, metallic NPs such as Au, Ag, Pd, Pt, and CuO act as heterogeneous catalysts, which invoke accelerated reactions on their surface compared to homogeneous reactions in the liquid phase. Typical reactions catalyzed by metallic NPs are redox processes, in which a NP catalyst, upon adsorbing reactant molecules (or ions in a solution), transfers electrons from a reductant to an oxidant. Inasmuch as metallic NPs are used to catalyze desired redox reactions, a well-controlled redox reaction can be used to detect metallic NPs of interest.

A suitable redox reaction is the reduction of tetramethylthionine chloride (methylene blue or MB) by sodium borohydride ($NaBH_4$). $NaBH_4$ reduces chemicals including p-nitrophenol, ferrocyanate, and MB, among which MB can be sensitively detected by a regular absorbance spectrometer ($\lambda_{max}$=663-665 nm). Reduction of MB by $NaBH_4$ is slow in the absence of any catalyst, providing a favorable NP-free background.

Figure 1:
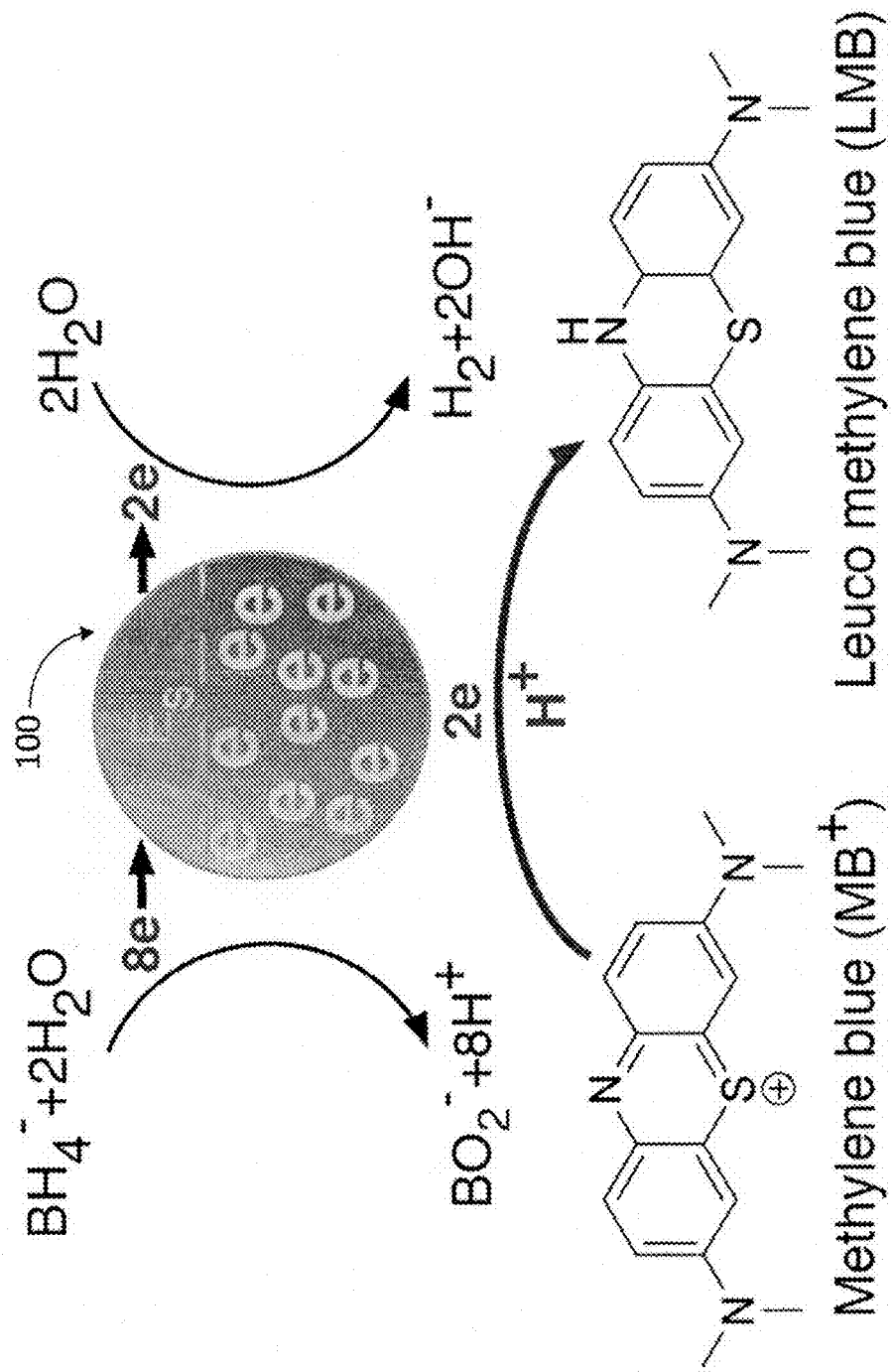
FIG. 1 depicts reduction of methylene blue (MB) to leuco methylene blue (LMB) the presence of a metallic nanoparticle (NP).

The heterogeneous catalytic processes on the NP surface can be described by an electrochemistry-guided kinetic model. FIG. 1 depicts the hydrolysis of borohydride and the reduction of MB, with NP 100 storing electrons as an electrode on which MB is reduced. Leuco methylene blue (LMR) may be oxidized by dissolved oxygen (not shown).

In one embodiment, a powder assay includes $NaBH_4$, MB, and HEPES in the form of a powdered mixture. The powder assay has final working solution containing about 20 μM MB, about 10 mM HEPES buffer at pH 7, and about 10 mM $BH_4^-$. This results in a $NaBH_4$:HEPES:MB molar ratio of about 500:500:1. In some embodiments, the powder assay includes a base, such as sodium hydroxide. The powder assay, when dissolved in water, has a pH of about 7.

An assay kit typically includes a vial containing the powder assay. The vial is may be formed of an optically transparent material suitable for use as a cuvette in a spectrophotometer. The vial may have a pathlength in a range of about 0.1 cm to about 5 cm. Absorbance range sensitivity of the spectrophotometer is typically in a range of about 0.0001 $cm^{-1}$ to about 0.01 $cm^{-1}$, with lower absorbance range sensitivity having lower NP detection limits. The assay kit can be used to detect NPs having a concentration in a range of about 5 μg/L to about 500 μg/L or greater (e.g., about 1000 μg/L). In some embodiments, a "low range" assay kit is suitable for detection of NPs in a range of about 0.1 μg/L to about 10 μg/L, and a "high range" assay kit is suitable for detection of NPs in a range of about 5 μg/L to about 1000 μg/L. The low range assay kit and the high range assay kit may differ, for example, in pathlength of the vial, with other differences in implementation, including different sample sizes and optical sensors.

In one example, an assay kit includes 0.28 g of chemical powder to be combined with 10 mL of aqueous solution (sample) and responds linearly to metallic NP concentration through the absorbance after 2 minutes of reaction, showing a detection limit of 20 μg/L for 20 nm Au NPs having an active surface. The overall assay reaction kinetics can be modeled by taking account of surface charge transfer on metallic NPs and the competition of MB reduction with $BH_4^-$ hydrolysis and LMB oxidation. It is believed that metallic NPs store electrons as microelectrodes, where MB is reduced, suggesting enhanced performance of the assay kit for conductive materials over insulating materials. Parameters obtained by fitting experimental data with this model allow robust designs of the powder assay kits for broad sample characteristics.

The powder assay may be prepared by combining MB, HEPES, and water to yield an aqueous mixture, removing water from the aqueous mixture to yield a solid mixture, and combining $NaBH_4$ in solid (e.g., powder) form with the solid mixture to yield the powder assay. The water may be removed, for example, by freeze drying. $NaBH_4$ in solid form is combined with the solid mixture to avoid reaction of $NaBH_4$ with water in the aqueous mixture.

Detecting metallic nanoparticles in an aqueous solution is achieved by combining a powder assay as described herein with the aqueous solution to yield a test solution, and assessing a concentration of the metallic nanoparticles in the test solution based on absorbance of light (e.g., at 663 nm) by the test solution. A concentration of MB in the test solution is typically in a range of 20 μM, a concentration of HEPES in the test solution is typically in a range of 10 mM, and a concentration of the $NaBH_4$ in the test solution is typically in a range of 10 mM. The metallic nanoparticles catalyze the reduction of MB to LMB by $NaBH_4$.

The concentration of the metallic nanoparticles in the test solution may be assessed less than five minutes after (e.g., two minutes after) combining the powder assay with the aqueous solution. For example, gold metallic nanoparticle concentrations in a range of 5 μg/L for 5-nm Au NP (equivalent to a reactive NP surface area of 0.3 $m^2/m^3$) are detectable using the powder assay. Assessing the concentration of the metallic nanoparticles typically includes comparing $\Delta A^{663}$ (the absorbance difference at 663 nm between a test solution and a blank) with $A^{663}$ solutions having known concentrations and sizes of metallic nanoparticles.

In one embodiment, an assay kit including a dry powder containing MB, $NaBH_4$, and HEPES buffer allows detection of metallic NPs within two minutes. $\Delta A^{663}$ is linearly and reproducibly correlated to the NP surface area concentration. In one example, a detection limit of the powder assay is 0.32 $m^2/m^3$ of equivalent surface area of metallic NPs, or 1 μg/L for 1-nm metallic NPs, demonstrating its advantage for detecting small NPs at trace levels in water.

The powder assay can be used to quantify NP species in water, including Au, Ag, Pd, Pt, and CuO, and evaluate the surface catalytic reactivity order of them. The powder assay may also be used to provide the "total catalytic reactivity of NPs" (TCRN) in a water sample containing "unknown" NP species, serving as a tool to directly probe the NP reactivity potential that is relevant to the environmental health and safety of nanomaterials.

Applications of this powder assay include use as a rapid indicator to track known NPs (e.g., Au NPs) throughout reactors (e.g., environmental systems, biota) and use to detect "unknown" particles in water as the TCRN, an indicator of the surface catalyzing potential of particles. Thus, the assay may also be useful to increase understanding of how environmental conditions (e.g., sulfidation or natural organic matter) passivate NP surfaces or, as illustrated by the difference between filtered and unfiltered surface water, demonstrate the relative presence of surface catalyzing particles present in water systems.

EXAMPLES

Materials. Methylene blue hydrate (≥95%, product #28514), sodium borohydride ($NaBH_4$, ≥98%, product #452173), HEPES (≥99.5%, product #H3375), and sodium hydroxide (NaOH, 99.99% trace metal basis, product

306576) were purchased from Sigma-Aldrich and used without further purification. Gold nanospheres (NanoXact, 0.05 mg/mL) with nominal sizes of 20 nm, 50 nm, and 80 nm, were purchased from nanoComposix. According to the manufacturing information, these Au NPs are coated with tannic acid on the surface and suspended in solution with pH of 5.1-5.4, giving negative zeta-potential (−44 mV for 20 nm, −54 mV for 50 nm and 80 nm). Palladium (Pd) and platinum (Pt) NP samples were adopted from two commercial products designed as human dietary supplement drinks. A copper oxide (CuO) nanopowder (Sigma-Aldrich, 544868, <50 nm, average size 28 nm, specific surface area 33 m$^2$/g) was dispersed in ultrapure water to make a stock solution (1 g/L).

Ultrapure water (18.2 MΩ·cm, Barnstead GenPure xCAD Plus) was used to make all solutions unless stated otherwise. Surface water sample was collected from Colorado River and a portion was filtered (pore size 1.6 μm, Whatman GF/A, 1820-025). The filtered surface water contained 3.9 mg/L of dissolved organic carbon (DOC) and had a UV absorbance of 0.074 at 254 nm (UV254). A Suwannee River Natural Organic Matter (SRNOM) sample (2R101N, IHSS) was used as a model Natural Organic Matter (NOM) compound. The percentage of carbon (C) by mass of this SRNOM was 50.7% according to IHSS, and 47.0% (used in this analysis) according to total organic carbon (TOC) analysis.

Powder Assay Synthesis. The powder assay was designed to achieve a final working solution containing 20 μM MB, 10 mM HEPES buffer at pH 7, and 10 mM $BH_4^-$. This corresponds to a $NaBH_4$:HEPES:MB molar ratio of 500:500:1. To achieve a homogeneous powder mixture, 0.06 g MB, 22.35 g HEPES, and 0.8 g NaOH (to raise the pH of HEPES buffer to 7 in the final solution) were dissolved into ~100 mL ultrapure water, and the resulting solution was frozen and then freeze dried (Labconco FreeZone Console Freeze Dry System, 6 Liter) at a collector temperature <−40° C. and vacuum <0.45 mBar for 72 hours. After freeze drying, the powder was ground using mortar and pestle to achieve a visually uniform and fine powder. Because $NaBH_4$ reacts with water, it was not included in the freeze-dried mixture, but was directly ground in a mortar to achieve a fine powder. The two powders were well mixed at a mass ratio of 6.54:1 (converted from the molar ratio) in a glass vial using a vortex mixer, yielding the final reagent powder. As an assay kit, 0.28 g of the final powder was added to a clear glass vial designed for absorbance measurement (COD digestion vials, HACH product #2125815).

Powder assay procedure. For each powder assay, a 10 mL sample was added into one assay vial prepared as described previously, and a timer was started. Immediately after adding the sample to the vial, the acute dissolution and hydrolysis of $NaBH_4$ in water formed hydrogen gas bubbles. The rapidly generated bubbles assisted a fast diffusion of MB and achieved a homogeneous solution with a uniform blue color in a few seconds. The sample vial was gently and repeatedly inverted to maintain constant mechanical mixing of the solution and drive the hydrogen bubbles into the gas phase in the vial. After 2 min, the vial was placed in an absorbance spectrometer (DR5000, HACH) to measure the visible light absorbance at 663 nm.

Solution-based $BH_4^-$-MB assay using time resolved UV-VIS spectrometry. Solution-based methods were used to complement and validate the above dry powder kit methodology. 2.5 mL of prepared 10 mM HEPES buffer (pH=7) was added into a 1-cm polystyrene cuvette (Perfector Scientific, #9012). MB stock solution (4 mM) was added to reach a final concentration of 20 μM. The cuvette was then placed in a portable UV-VIS spectrometer (Ocean Optics, USB-ISS-UV/VIS and USB4000 light source), which was positioned on a magnetic stirring plate (IKA, Lab DISC). The solution in the cuvette was mixed with a magnetic micro stir bar (VWR Spinbar, 1.5×7.9 mm). While mixing, 12.5 μL of $NaBH_4$ stock solution (1 M, prepared in 1 mM NaOH in an ice bath to minimize hydrolysis) was added into the cuvette to achieve an initial $BH_4^-$ concentration of 5 mM. The spectrometer was operated in a time resolved reading mode to acquire absorbance at both 663 nm ($A^{663}$) and 760 nm ($A^{760}$) every 0.1 s. The analysis reaction for an analysis was initiated directly in the cuvette by adding Au NP stock solution in a desired concentration. The moment Au NP was added, absorbance at 663 nm started dropping over time. Time-resolved $A^{663}$ and $A^{760}$ data were saved for 20 min from the Au NP spiking point and then exported for further analysis.

$A^{663}$ was recorded to quantify MB concentration, whereas $A^{760}$ was recorded to monitor light scattering caused by the hydrogen gas bubbles. A subtraction of $A^{760}$ from $A^{663}$ corrected the $A^{663}$-time spectrum ($A^{663}$ versus time) to reflect only MB reduction.

The corrected $A^{663}$-time spectrum was then converted to kinetic data showing MB concentration versus time, using an experimentally assessed extinction coefficient of 74663 L·mol$^{-1}$·cm$^{-1}$ for MB. The kinetics data were fitted by a model using the non-linear regression toolbox of MATLAB (R2015b). All model calculation and simulation were also employed in MATLAB involving the use of its ordinary differential equation solver package.

Figure 2A:
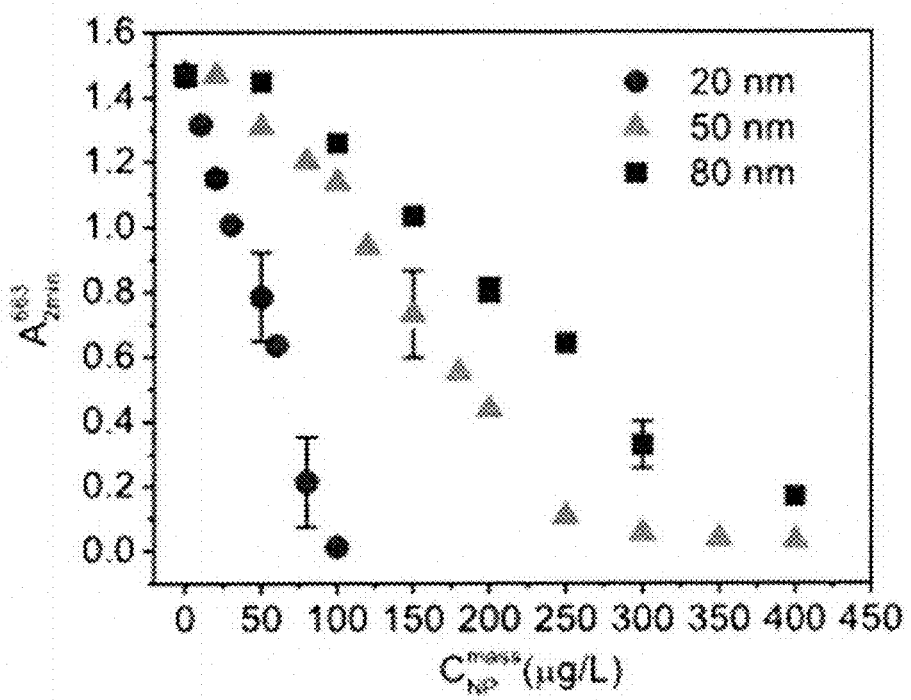
FIGS. 2A and 2B show assay evaluation by Au NPs of three sizes.

Assay Evaluation with Au NPs. The powder assay was applied to Au NPs of three different sizes (20, 50, and 80 nm) suspended in ultrapure water. For each NP size, $A_{2min}^{663}$ suggests the remaining MB concentration after the reaction, showing an inverse and linear correlation to the NP mass concentration ($C_{NP}^{mass}$), as shown in FIG. 2A. The corresponding slope (the absolute value) in FIG. 2A varied among the three sizes in the order 20 nm>50 nm>80 nm, indicating the assay was more sensitive to smaller NPs. Based on the principle heterogeneous catalysis, the steeper slope of smaller size NPs is attributed to the larger surface area. To verify this, $\Delta A^{663}$ (the difference of $A_{2min}^{663}$ between a blank (i.e., ultrapure water without NPs) and a sample) over the surface area concentration (i.e., surface area per volume of solution) of equivalent Au NPs ($C_{Au-eqv}^{surface}$ in m$^2$/m$^3$). $\Delta A^{663}$ across different NP sizes shows a single linear correlation to $C_{Au-eqv}^{surface}$ validating the principle of heterogeneous catalysis.

Figure 2B:
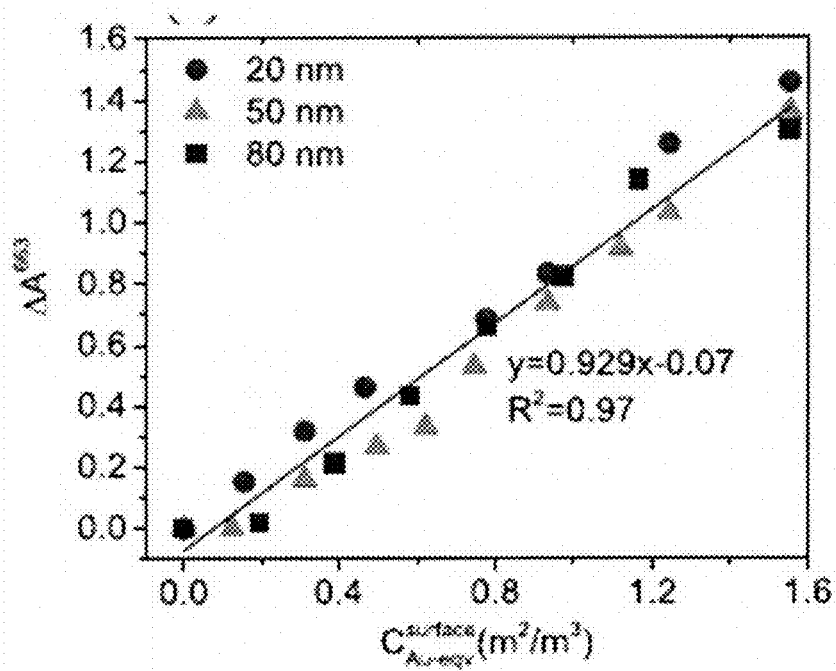

A 50 nm Au NP solution (80 μg/L) was analyzed in 8× replication to determine the method detection limit (MDL) of the assay. The MDL was calculated using 2.998 ($t_{0.99,n=7}$)×σ (standard deviation) and the experimental calibration curve of FIG. 2B following a method recommended by the United States Environmental Protection Agency (Agency, U.S.E.P., Definition and Procedure for the Determination of the Method Detection Limit, Revision 2 In Water, O. o., Ed. 2016), which is incorporated by reference herein. The MDL was determined to be 0.31 m$^2$/m$^3$ as $C_{Au-eqv}^{surface}$. The MDL can be converted to $C_{MP}^{mass}$ for different NP sizes for spherical Au NPs (density= 19.3 g·cm$^{-3}$). The essential surface correlation of the assay determines that the method has lower mass-based MDL for smaller sizes. The assay is expected to sensitively detect 1-nm Au NPs at ~1 μg·L$^{-1}$. The MDL for 50 nm Au NPs was determined to be ~50 1 μg·L$^{-1}$ by the powder assay.

Figure 3:
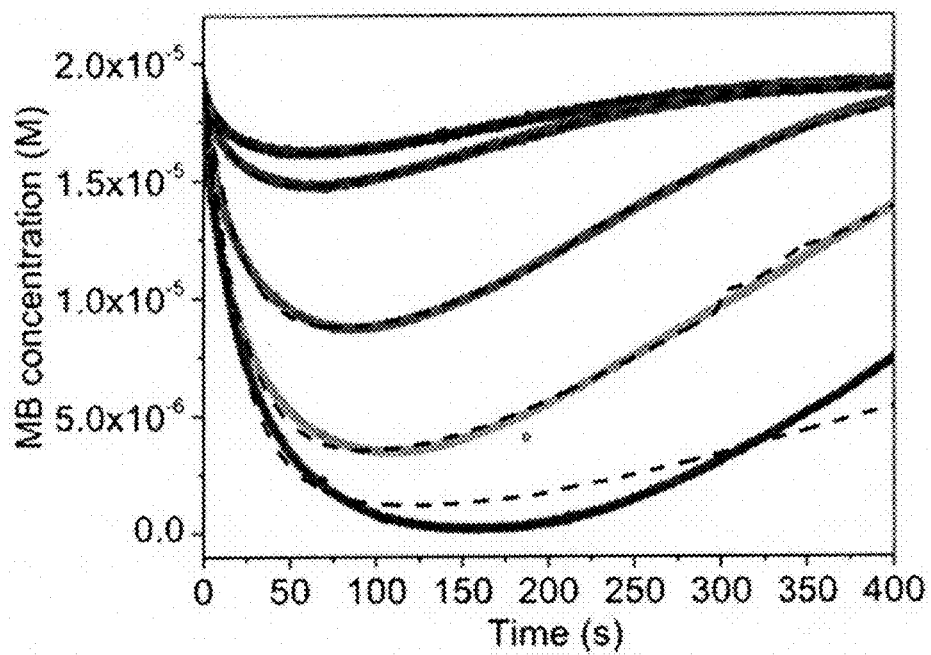
FIG. 3 shows MB reaction kinetics (concentration versus time) in the presence of Au NPs at 50 100, 160, 200, and 250 µg/L, sampled every 0.1 s using time-resolved ultraviolet-visible (UV-VIS) spectroscopy.

Assay Reaction Mechanism Analysis. During the reactions of the powder assay kit, $BH_4^-$ (10 mM in a working solution) is in excess compared to MB (40 or 20 μM). If the reduction of MB by $BH_4^-$ was the only dominant reaction, one would observe decay MB to zero after a sufficiently long reaction time; however, the observed reaction "equilibrium" suggested other reactions happening opposing MB reduction. To improve understanding of the reaction mechanism, MB reduction kinetics were investigated using wet chemicals (i.e., as solutions) in solution-based and time-resolved UV-VIS spectrometry. MB concentration decayed to a minimum in 50-100 seconds, remained in steady state at the minimum for about tens of seconds, and appeared to reform until reaching an $A^{663}$ near the initial level, as shown in FIG. 3. FIG. 3 also reveals that higher Au NP dosage leads to a faster MB reduction rate and lower equilibrium level. However, despite faster reaction rate initially, it took longer time for higher Au NP dosage to reach the equilibrium, which opposes typical behavior of one-step reactions where faster reaction rates reach equilibrium in shorter time, thus suggesting the reaction(s) against MB reduction is not merely a back oxidation.

MB is reduced to LMB in the assay reaction, as confirmed by an absorbance peak at ~254 nm. LMB can be oxidized by molecular oxygen and reform MB. $BH_4^-$ also reacts with water in room temperature, and the hydrolysis is favored in neutral and acidic conditions. It is believed that these are the two major reactions going against MB reduction. Thus, reactions in the system may be summarized as:

$$BH_4^- + 2H_2O \rightarrow BO_2^- + 4H_2 \quad (1)$$

$$BH_4^- + 4MB^+ + 2H_2O \rightarrow BO_2^- + 4LMB + 4H^+ \quad (2)$$

$$2LMB + O_2 \rightarrow 2MB^+ + 2OH^- \quad (3)$$

where $MB^+$ is the cation species of MB ($pK_a=0$). Reaction (1) can happen both in bulk solution (homogeneous reaction) and on NP surface (heterogeneous reaction). Reaction (2) is the primary reaction enabling the assay and happens all or substantially all on the NP surface.

Half reactions on Au NP surface composing reaction (1) and (2) are believed to include:

$$BO_2^- + 8H^+ + 8e \rightarrow BH_4^- + 2H_2O \quad k_1^0 E_1^0 \quad (4)$$

$$2H_2O + 2e \rightarrow H_2 + 2OH^- \quad k_2^0 E_2^0 \quad (5)$$

$$MB^+ + 2e + H^+ \rightarrow LMB \quad k_3^0 E_3^0 \quad (6)$$

where $k_1^0$, $k_2^0$, and $k_3^0$ are standard rate constants, and $E_1^0$, $E_2^0$, and $E_3^0$ are standard or formal potentials for reactions (4) to (6). Reaction (4) is anodic and reactions (5) and (6) are cathodic.

Figure 4A:
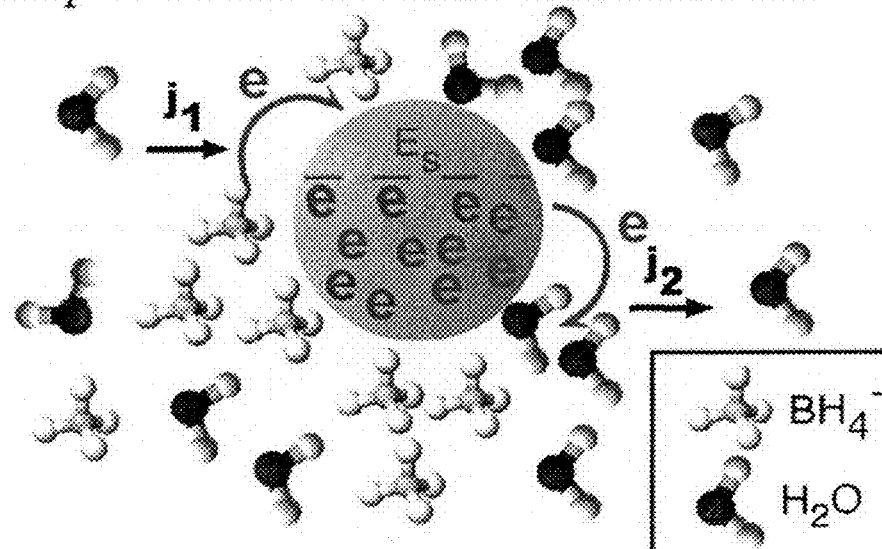
FIGS. 4A and 4B depict proposed kinetic steps of reactions that occur on the NP surface.
Figure 4B:
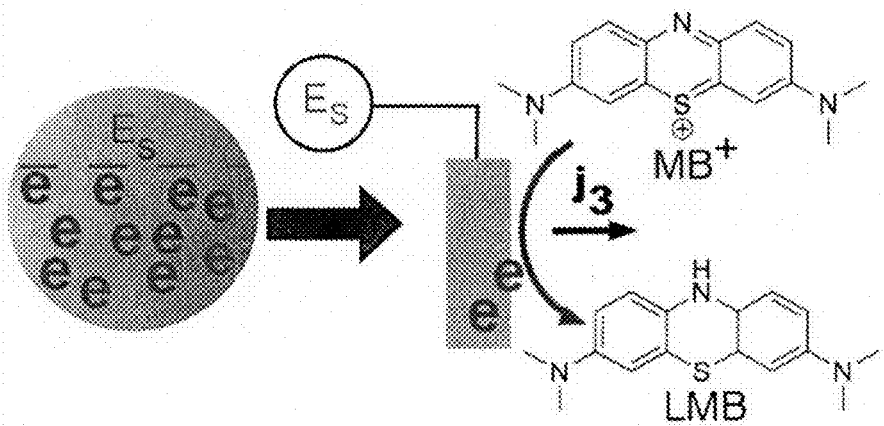

Two reaction steps, depicted in FIGS. 4A and 4B, respectively, were hypothesized for the assay. In Step 1 (FIG. 4A), Au NPs were instantly charged with electrons from the strong reductant, $BH_4^-$, giving anodic current density of $j_1$. This process is diffusion-controlled and takes place in a few milliseconds estimated from the diffusion coefficient of $BH_4^-$ ($1.6 \times 10^{-5}$ cm$^2$/s). Reaction (1) in solution is much slower (scale of minutes) than on NP surfaces (scale of milliseconds), and therefore dominates $BH_4^-$ concentration. Meanwhile, electrons stored on Au NPs were discharged via reaction (5), giving cathodic current density of $j_2$. When the charging and discharging rate counterbalanced each other (i.e., $j_1+j_2=0$), a steady state potential ($E_S$) was established on the NPs, establishing an electrode with potential $E_s$. Contribution to $j_2$ by reaction (6) is neglected in Step 1 because water was in excess compared with MB and was not limited by mass transfer. In Step 2, the electrode reduction of MB (reaction (6)) takes place in response to $E_s$, giving cathodic current density $j_3$. The separation of Step 1 and Step 2 is validated because the time scale for establishing $E_s$ (at milliseconds) was thousands of times shorter than that of reaction (6) (at tens of seconds estimated from FIGS. 4A and 4B).

Figure 5:
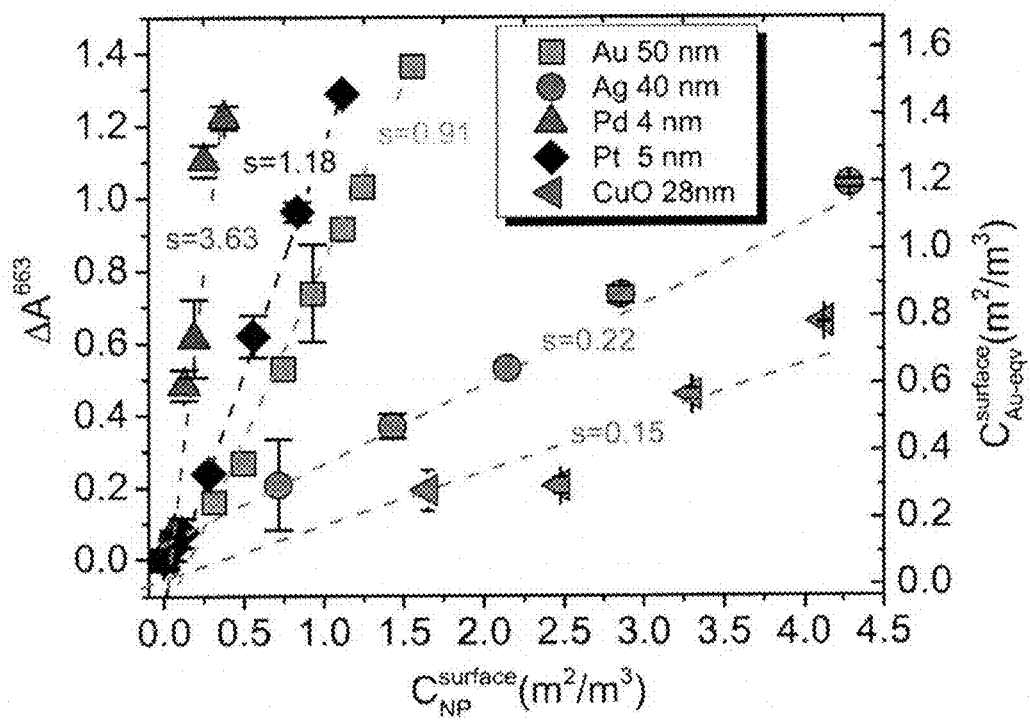
FIG. 5 shows calibration curves for gold (Au), silver (Ag), palladium (Pd), platinum (Pt), and copper oxide (CuO) NPs.

This powder assay, based on a well-defined heterogeneous catalysis process can facilitate the environmental analysis of metallic NPs with surface catalytic reactivity. First, it can quantify one species of NP in a consistent water matrix. For this purpose, calibration curves correlating the assay's response (i.e., $\Delta A^{663}$) to NP concentrations were prepared. The calibration curves of Au, silver (Ag), palladium (Pd), platinum (Pt), and copper oxide (CuO) in ultrapure water matrix are shown in FIG. 5. The assay's response (i.e., $\Delta A^{663}$) to the NP concentration was shown to be directly related to the surface reaction rate, estimated from (providing known specific surface area) and chosen as the x-axis. For Au, Ag, Pt, and Pd NPs, the specific surface area was estimated by assuming all the NPs are spherical and have the density of the corresponding bulk materials. For the CuO NPs, the specific surface area was provided by the manufacturer. The calibration curve varied, reflected from the different slope, among the five NP species, suggesting the catalytic surface reactivity order as Pd>Pt>Au>Ag>CuO. The selected five metallic (metal or metal-like) NPs demonstrated catalytic activity in specific reactions. A systematic comparison of the catalytic reactivity of the different metallic materials with the same reaction was not found. It was expected that CuO would have the lowest surface catalytic reactivity because of being an oxide material, which has lower electron mobility than metals in general. Findings suggested that Au has higher surface-normalized catalytic reactivity than Ag. With each calibration curve in FIG. 5, the concentration of one NP species can be estimated by measuring $\Delta A^{663}$ using the powder assay.

Figure 6:
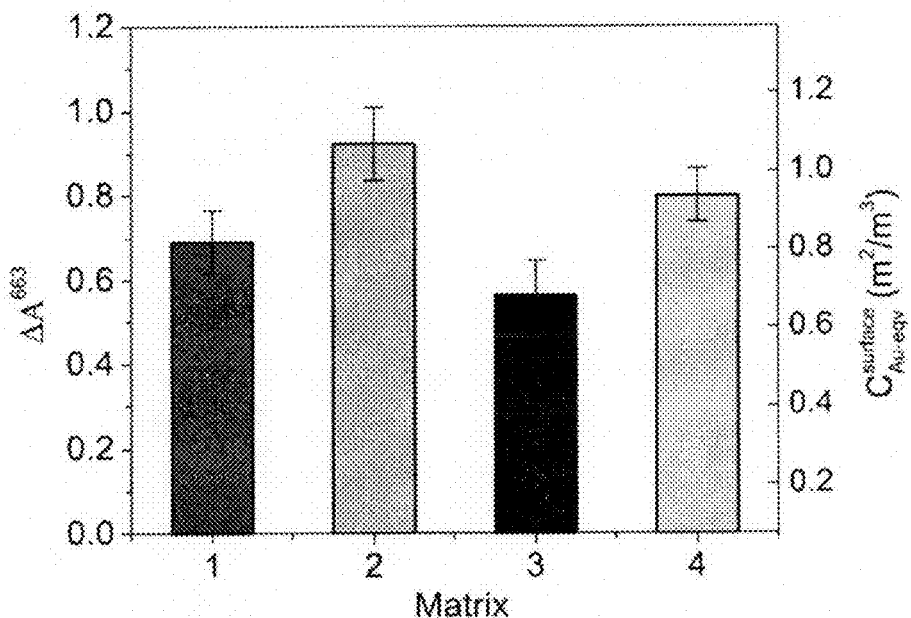
FIG. 6 shows total catalytic activity of NPs (TCRN) analyzed by the powder essay for 150 µg/L Au NPs (50 nm) suspended in ultrapure water (Matrix 1), surface water (Matrix 2), filtered surface water (Matrix 3), and water containing Suwannee River Natural Organic Matter (0.5-10 mg/L as C, Matrix 4).

The powder assay can detect the total catalytic reactivity of NPs (TCRN) in an environmental water sample. As examples, the analyses of 150 μg/L Au NPs (50 nm) suspended in ultrapure water (Matrix 1), surface water (Matrix 2), filtered surface water (Matrix 3), and water containing SRNOM in the range 353 of 0.5-10 mg/L as C (Matrix 4). FIG. 6 presents the outcomes in $\Delta A^{663}$ and in $C_{Au-eqv}^{surface}$ (calibrated by FIG. 2B). Compared against Matrix 1, Matrix 2 showed higher TCRN (p<0.05), suggesting the presence of other catalytically reactive compounds, which are likely also metallic colloids, other than the spiked Au NPs. Matrix 3 and Matrix 4 showed statistically insignificant variance from Matrix 1 (p>0.05), suggesting that the reactive compounds in the surface water were effectively removed by the glass fiber filter and the dissolved NOM puts negligible impact on the surface catalytic reactivity of Au NPs. This was further proved by assay tests with Au NPs suspended in water containing different levels of Suwanee River NOM. TCRN can be closely related to NP toxicity and fate in environmental waters, and thus critical to the environmental health and safety (EHS) of nanomaterials.

A number of embodiments have been described. Nevertheless, it will be understood that various modifications may be made without departing from the spirit and scope of the disclosure. Accordingly, other embodiments are within the scope of the following claims.

What is claimed is:

1. A composition comprising:
    sodium borohydride ($NaBH_4$);
    methylene blue (MB); and
    4-(2-hydroxyethyl)-1-piperazineethanesulfonic acid (HEPES),
    wherein the composition is in the form of a powdered mixture.

2. The composition of claim 1, wherein a molar ratio of $NaBH_4$:HEPES:MB is about 500:500:1.

3. The composition of claim 1, further comprising a base.

4. The composition of claim 3, wherein the base is sodium hydroxide.

5. The composition of claim 4, wherein the composition, when dissolved in water, has a pH of about 7.

6. An assay kit comprising:
    a vial containing a composition comprising:
        sodium borohydride ($NaBH_4$);
        methylene blue (MB); and
        4-(2-hydroxyethyl)-1-piperazineethanesulfonic acid (HEPES),
        wherein the composition is in the form of a powdered mixture.

7. The assay kit of claim 6, wherein a molar ratio of $NaBH_4$:HEPES:MB in the composition is about 500:500:1.

8. The assay kit of claim 6, wherein the composition further comprises sodium hydroxide.

9. The assay kit of claim 8, wherein the composition, when dissolved in water, has a pH of about 7.

10. A method of forming a composition for detecting metallic nanoparticles in aqueous media, the method comprising:
    combining methylene blue (MB), 4-(2-hydroxyethyl)-1-piperazineethanesulfonic acid (HEPES), and water to yield an aqueous mixture;
    removing water from the aqueous mixture to yield a solid mixture; and
    combining sodium borohydride ($NaBH_4$) powder with the solid mixture to yield the composition, wherein the composition is in the form of a powder.

11. The method of claim 10, wherein removing the water from the aqueous mixture comprises freeze-drying the aqueous mixture.

12. A method of detecting metallic nanoparticles in an aqueous solution, the method comprising:
    combining a composition with the aqueous solution to yield a test solution, wherein the composition comprises:
        sodium borohydride ($NaBH_4$);
        methylene blue (MB); and
        4-(2-hydroxyethyl)-1-piperazineethanesulfonic acid (HEPES),
        wherein the composition is in the form of a powdered mixture; and
    assessing a concentration of the metallic nanoparticles in the test solution based on absorbance of light by the test solution.

13. The method of claim 12, comprising assessing the concentration of the metallic nanoparticles in the test solution less than five minutes after combining the composition with the aqueous solution.

14. The method of claim 12, wherein a concentration of MB in the test solution is about 20 µM.

15. The method of claim 12, wherein a concentration of HEPES in the test solution is about 10 mM.

16. The method of claim 12, wherein a concentration of the $NaBH_4$ in the test solution is about 10 mM.

17. The method of claim 12, wherein assessing the concentration of the metallic nanoparticles comprises assessing a concentration in range of about 5 µg/L to about 500 µg/L for 5-nm gold nanoparticles.

18. The method of claim 17, wherein the concentration of 5 µg/L for 5-nm gold nanoparticles is equivalent to a reactive nanoparticle surface area of about 0.3 $m^2/m^3$.

19. The method of claim 12, wherein assessing the concentration of the metallic nanoparticles comprises comparing the absorbance of light having a wavelength of 663 nm by the test solution with the absorbance of light having a wavelength of 663 by solutions having known concentrations of the metallic nanoparticles.

20. The method of claim 12, wherein the metallic nanoparticles catalyze reduction of MB to leuco methylene blue (LMB).

* * * * *